United States Patent [19]

Hetherington et al.

[11] 4,068,523

[45] Jan. 17, 1978

[54] NON-DESTRUCTIVE TESTING

[75] Inventors: Matthew J. Hetherington, near Market Harborough; Richard Lewis, Rushden; Graham E. Goode, Corby, all of England

[73] Assignee: British Steel Corporation, London, England

[21] Appl. No.: 643,685

[22] Filed: Dec. 23, 1975

[30] Foreign Application Priority Data

Dec. 31, 1974 United Kingdom ............... 56193/74

[51] Int. Cl.² ............................................. G01N 29/04
[52] U.S. Cl. .................................................... 73/628
[58] Field of Search .............. 73/67, 67.5 R, 67.7, 73/67.8 R, 67.9, 71.5 US, 12

[56] References Cited

U.S. PATENT DOCUMENTS

| 2,601,779 | 7/1952 | Firestone | 73/67.8 R |
| 3,067,605 | 12/1961 | Bliss | 73/67 |
| 3,132,510 | 5/1964 | Buchan et al. | 73/67.7 |
| 3,224,253 | 12/1965 | McKay | 73/67 |
| 3,391,571 | 7/1968 | Johanson | 73/67 |
| 3,521,483 | 7/1970 | Miller et al. | 73/67.5 R |
| 3,788,466 | 1/1974 | Wilson | 73/12 |

*Primary Examiner*—Richard C. Queisser
*Assistant Examiner*—Stephen A. Kreitman
*Attorney, Agent, or Firm*—Bacon & Thomas

[57] ABSTRACT

An arrangement for the non-destructive testing of articles in which a head, carrying at least one ultrasonic testing transducer, is caused to reciprocate so as to impact upon the article to be tested with an impulsive blow of short dwell time once during each reciprocation, the transducer element carrying out a testing operation during the dwell time of each impact.

15 Claims, 2 Drawing Figures

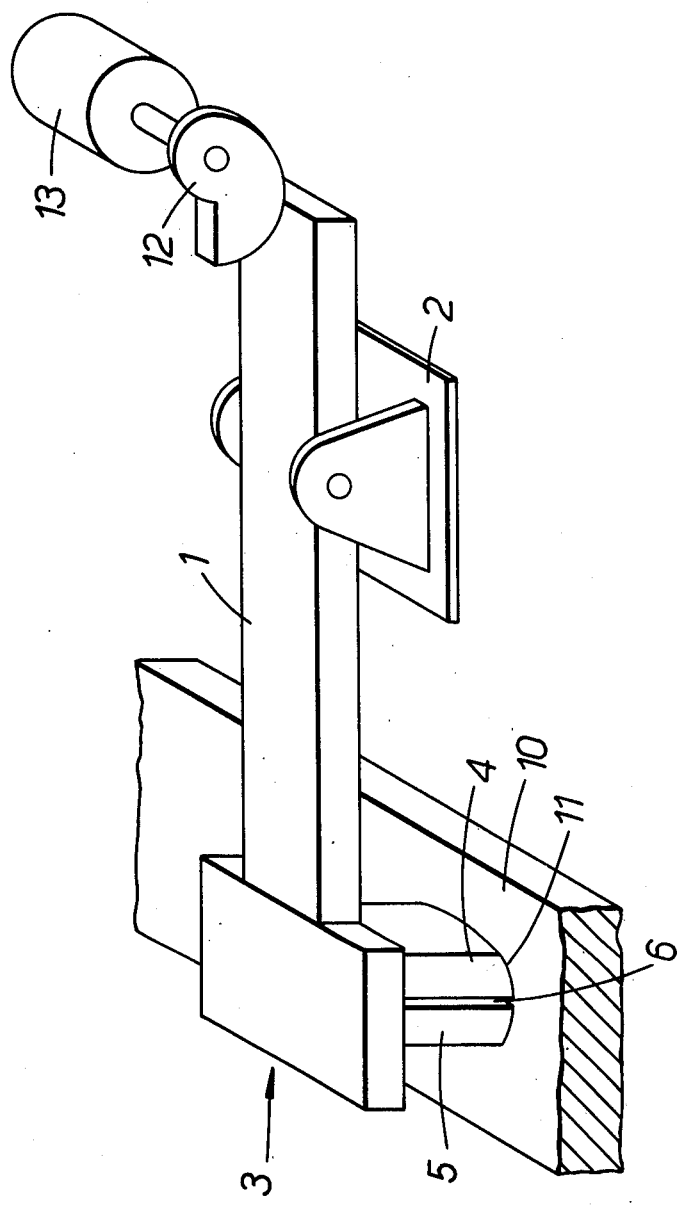

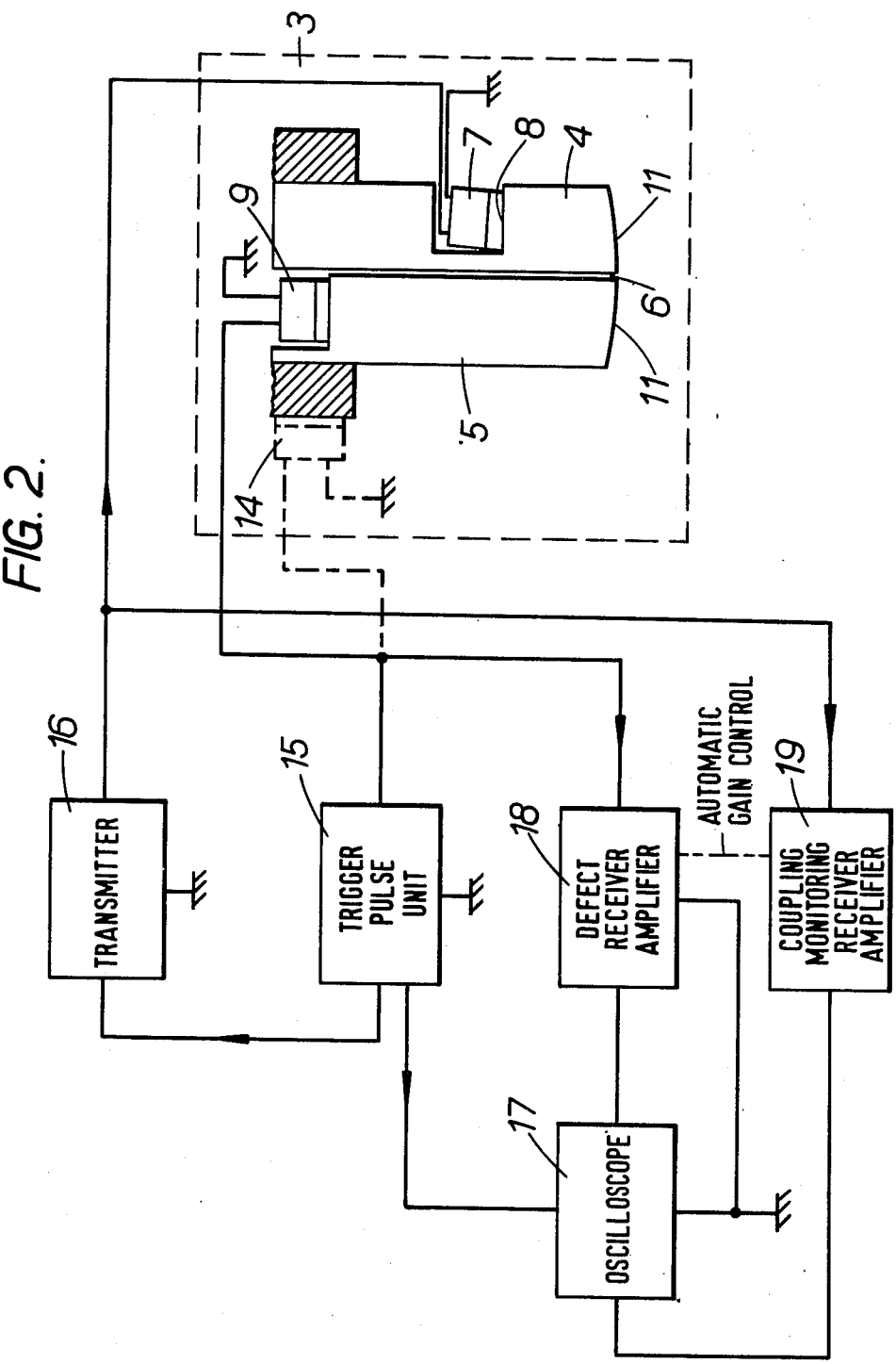

NON-DESTRUCTIVE TESTING

This invention relates to non-destructive testing and more particularly to non-destructive testing of articles by means of ultrasonic transducer elements.

According to one aspect of the invention there is provided apparatus for the non-destructive testing of articles comprising a head mounted for reciprocating movement; an ultrasonic testing transducer element mounted on the head; means for reciprocating the head such that in use the head is caused to impact upon the article to be tested with an impulsive blow of short dwell time once during each reciprocation of the head; and means for actuating the transducer element for testing operation during the dwell time of each impact.

According to another aspect of the invention there is provided a method of non-destructively testing articles comprising repeatedly impacting a head carrying an ultrasonic transducer element with an impulsive blow of short dwell time upon different portions of an article to be tested, and actuating the transducer element for testing operation during the dwell time of each impact.

In one embodiment of the invention the head is carried by and movable with a lever member pivotally mounted on a fixed frame. In this case the reciprocation of the lever may be caused by any convenient means such as by means of a cam which lifts the lever and then permits it to fall towards the article to be tested dispose there below.

A single testing transducer may be used both for transmitting ultrasonic pulses into the article to be tested and for receiving echoes of the transmitted pulses from the article to be tested. Alternatively the head may carry separate testing transducer elements for the transmission of pulses and for the reception of pulse echoes. In this case, in order to reduce the problems of direct acoustic coupling between the two testing transducers, they may be mounted on separate parts of the head spaced apart by an air gap or an acoustic attenuator.

The means for actuating the transducer element may comprise a triggering transducer element mounted on the head and connected in an electrical circuit such as to trigger operation of the testing element or elements upon detection of the impact of the head on the article to be tested.

The short dwell time may be less than 0.001 seconds and may be of the order of 0.00025 to 0.0005 seconds.

A coupling monitoring provision may be included in the method and apparatus according to the invention. Thus there may be provided a means for measuring the amount of sound wave energy coupled into the workpiece for each impact, and to use this measurement to control the sensitivity of a defect signal receiver amplifier such that the larger the ultrasonic energy transmitted into the workpiece, the lower the sensitivity of the defect signal amplifier. In this manner a particular defect in the workpiece produces a signal of similar amplitide after the defect receiver amplifier which is essentially independent of the ultrasonic energy coupled into the workpiece.

The invention is particularly applicable to the testing of hot articles such as hot metal (e.g. steel) billets, where the invention enables the provision of good sonic contact between the head and the billet during the dwell time of impact without requiring the presence of a sonic coupling liquid, and where the short dwell time of contact of the head on the billet prevents overheating of the head which could be detrimental to the transducer element or elements.

In order that the invention may be more readily understood one embodiment thereof will now be described by way of example with reference to the accompanying drawing in which:

FIG. 1 is a diagrammatic perspective view of apparatus for the non-destructive testing of steel billets; and FIG. 2 is a block diagram showing the electrical circuit for the operation of the apparatus of FIG. 1.

In the drawings there is shown a lever arm 1 pivotally mounted on a fixed base plate 2, and carrying at one end a head assembly 3.

As shown most clearly in FIG. 2 the head assembly 3 includes two lead members 4 and 5 separated by an air gap 6, although the two parts could alternatively be separated by a suitable acoustic attenuator spacing member.

A transmitting testing ultrasonic transducer element 7 is mounted in a groove 8 in one member 4 of the head assembly 3, although in an alternative arrangement this transmitting element can be mounted on the upper surface of the member 4. A similar ultrasonic transducer 9 is mounted on the upper surface of member 5 of the head assembly 3. This transducer element 9 is arranged as the receiving testing transducer. It is to be noted that the transmitting testing element 7 is inclined at a small angle to the horizontal such that pulses transmitted from element 7 in use will, after reflection in a workpiece 10 pass to receiving element 9 with due allowance for refraction at the head assembly/workpiece interface. In an alternative arrangement the receiving transducer element 9 can be mounted in a groove in member 5 and inclined at a small angle to the horizontal in a similar manner to transmitting element 7.

It is to be noted that the separation of the two members 4 and 5 of the head assembly 3 greatly reduces direct acoustic coupling between the elements 7 and 9, thereby reducing extraneous signals at receiving transducer 9.

The head members 4 and 5 are provided with domed lower faces 11 to reduce the area of contact with the workpiece, and thereby increase the effect of the impulsive blow.

A snail cam 12 driven by a motor 13 is provided for turning the lever arm 1 about its pivot such as to raise the head assembly 3 and then allow it to fall with a hammertype impulsive blow upon the workpiece 10. Because of the domed nature of the lower faces 11 of the head members 4 and 5, the area of contact with the workpiece is small, but the impulsive nature of the blow (providing in one example a pressure of the order of 10,000 P.S.I during the dwell time) ensures that good sonic contact is made with the workpiece during the dwell time of the blow.

As shown in FIG. 2, a triggering transducer element 14 is mounted on the side of the head assembly 3. The output of the transducer 14 is connected to the input of a trigger pulse unit 15, the output of which in turn is connected to a pulse transmitter 16 and an oscilloscope 17. The output of the pulse transmitter 16 is of course connected to the transmitting testing transducer 7, whilst the output of the receiving testing transducer 9 is connected via a receiver amplifier 18 to the oscilloscope 17. The transmitting testing transducer 7 is also connected to a coupling monitoring receiver amplifier 19.

In operation the lever arm 1 is continuously reciprocated about its pivot by snail cam 12 so that the head assembly 3 repeatedly makes hammer blows upon the workpiece 10 (comprising in this case a hot steel billet at, for example, more than 1000° C). At the moment of each impact, transducer 14 detects the blow and triggers, via unit 15 and transmitter 16, the transmission of an ultrasonic pulse from transmitting element 7. At the same time in order to observe echo pulses from the workpiece the oscilloscope 17 is triggered.

The ultrasonic pulse emitted by transmitting element 7 travels via head member 4 to the head member/workpiece interface 11. At this point a part of the ultrasonic energy is transmitted into the workpiece and the remainder is reflected back into head member 4 and travels in the direction of the transmitting element 7. When this reflected ultrasonic wave is incident on the transmitting element 7, an electrical signal is generated and this travels to and is amplified by the Coupling Monitoring Receiver Amplifier 19. The Amplitude of this signal is related to the amount of ultrasonic energy coupled into the workpiece, and can thus be used to control the sensitivity of the Defect Receiver Amplifier 18. Thus automatic gain control of the Defect Receiver Amplifier 18 is provided to compensate for variations in ultrasonic coupling between head assembly and workpiece.

Receiving transducer element 9 then receives echo pulses indicative of faults in the billet 10 and/or the thickness of billet 10, these echo pulses being relayed as signals via amplifier 18 whose gain is adjusted dependent on the level of coupling. The signals from both receiver amplifiers 18 and 19 are displayed on the oscilloscope.

This total operation, of transmitting a single short ultrasonic pulse into the billet, and receiving echo pulses for each impact of the hammer is carried out during the dwell time of each contact of the head assembly 3 on the billet 10, which is of the order of 0.00025 to 0.0005 seconds.

Also during operation, the billet 10 is continuously moved past the testing apparatus, so that similar tests are carried out at a multiplicity of points along its length.

The defect and/or thickness echo signals can be fed into signal processing equipment of a known kind for providing a read out display sheet or equivalent data. Such processing equipment can be inserted in the circuit between amplifier 18 and oscilloscope 17.

We claim:

1. Apparatus for the non-destructive testing of articles comprising a head mounted for reciprocating movement; ultrasonic testing transducer means mounted on the head; means for reciprocating the head such that in use the head is caused to impact upon the article to be tested with an impulsive blow of short dwell time once during each reciprocation of the head; and means for actuating the transducer means for testing operation by the transmission of pulses and the reception of pulse echoes through the contacting area of the head and the article to be tested during the dwell time of each impact.

2. Apparatus as claimed in claim 1 wherein the head is carried by and movable with a lever member pivotally mounted on a fixed frame.

3. Apparatus as claimed in claim 2 wherein reciprocation of the lever is caused by means of a cam which in operation lifts the lever and then permits it to fall towards the article to be tested disposed therebelow.

4. Apparatus as claimed in claim 2 wherein the surface of the head which impacts the article to be tested is domed to reduce its impact surface area.

5. Apparatus as claimed in claim 1 wherein the head carries separate testing transducer elements for the transmission of pulses and for the reception of pulse echoes.

6. Apparatus as claimed in claim 5 wherein the transducer elements are mounted on separate parts of the head spaced apart by an air gap or an acoustic attenuator.

7. Apparatus as claimed in claim 5 wherein the means for actuating the transmission transducer element includes the reception transducer element which is connected in an electrical circuit such as to trigger operation of the transmission transducer element upon impact with the article to be tested.

8. Apparatus as claimed in claim 5 wherein the means for actuating the transducer element comprises a triggering transducer element mounted on the head and connected in an electrical circuit such as to trigger operation of the testing elements upon detection of the impact of the head on the article to be tested.

9. Apparatus as claimed in claim 1 including a defect signal receiver amplifier and means for measuring the amount of sound wave energy coupled into the article to be tested for each impact and controlling the sensitivity of the defect signal receiver amplifier in inverse ratio thereto.

10. A method of non-destructively testing articles comprising repeatedly impacting a head carrying ultrasonic transducer means with an impulsive blow of short dwell time upon different portions of an article to be tested, and actuating the transducer means for testing operation by transmission of pulses and the reception of pulse echoes through the contacting area of the head and the article to be tested during the dwell time of each impact.

11. A method as claimed in claim 10 wherein separate testing transducer elements are used for the transmission of pulses and for the reception of pulse echoes.

12. A method as claimed in claim 11 wherein detection of impact of the head upon the article to be tested by the reception transducer element is used to actuate the transmission transducer element for testing operation.

13. A method as claimed in claim 11 wherein impact of the head upon the article to be tested is detected by a triggering transducer element which is used to actuate the transmission transducer element for testing operation.

14. A method as claimed im claim 10 wherein the short dwell time is less than 0.001 seconds.

15. A method as claimed in claim 14 wherein the short dwell time is of the order of 0.00025 to 0.0005 seconds.

* * * * *